US010583265B2

(12) United States Patent
Whitcher et al.

(10) Patent No.: US 10,583,265 B2
(45) Date of Patent: Mar. 10, 2020

(54) PROPORTIONAL OXYGEN CONSERVING DEVICE WITH FLOW SENSING

(75) Inventors: Douglas Adam Whitcher, Atlanta, GA (US); Bradley Stewart Koeppel, Smyrna, GA (US); Bernhard Lewis Haberland, Palm City, FL (US); Jeremy Webster Blair, Atlanta, GA (US)

(73) Assignee: Koninklijke Philips N.V., Eindhoven (NL)

( * ) Notice: Subject to any disclaimer, the term of this patent is extended or adjusted under 35 U.S.C. 154(b) by 923 days.

(21) Appl. No.: 14/343,395

(22) PCT Filed: Sep. 7, 2012

(86) PCT No.: PCT/IB2012/054643
§ 371 (c)(1),
(2), (4) Date: Mar. 7, 2014

(87) PCT Pub. No.: WO2013/038319
PCT Pub. Date: Mar. 21, 2013

(65) Prior Publication Data
US 2014/0224246 A1   Aug. 14, 2014

Related U.S. Application Data

(60) Provisional application No. 61/533,871, filed on Sep. 13, 2011.

(51) Int. Cl.
*A61M 16/10*    (2006.01)
*B01D 53/04*    (2006.01)
(Continued)

(52) U.S. Cl.
CPC ...... *A61M 16/101* (2014.02); *A61M 16/0003* (2014.02); *A61M 16/0677* (2014.02);
(Continued)

(58) Field of Classification Search
CPC .............. A61M 16/101; A61M 16/204; A61M 16/0003; A61M 16/0677; A61M 16/10;
(Continued)

(56) References Cited

U.S. PATENT DOCUMENTS 4,516,424 A * 5/1985 Rowland ............... A61M 16/10
73/1.06
4,519,387 A    5/1985 Durkan
(Continued)

FOREIGN PATENT DOCUMENTS

CN    101534928 A    9/2009
CN    101636215 A    1/2010
(Continued)

*Primary Examiner* — Timothy A Stanis
*Assistant Examiner* — Victoria Murphy
(74) *Attorney, Agent, or Firm* — Michael W. Haas

(57) ABSTRACT

Methods and system for concentrating oxygen include providing a portable apparatus having a plurality of sieve beds, each sieve bed in the plurality of sieve beds including a first end and a second end, a reservoir storing oxygen-enriched gas exiting from the second ends of the plurality of sieve beds, a compressor, an oxygen delivery valve communicating with the reservoir via a delivery line, a flow sensor associated with the delivery line, and control electronics adapted to control operation of the oxygen delivery valve; measuring, via the flow sensor, a flow of the oxygen-enriched gas through the sensor and outputting a signal indicative thereof; and controlling, using the control electronics, the opening and closing the oxygen delivery valve to deliver the oxygen-enriched gas from the reservoir to a user based on the signal.

11 Claims, 7 Drawing Sheets

(51) Int. Cl.
  *C01B 13/02*  (2006.01)
  *A61M 16/06*  (2006.01)
  *A61M 16/00*  (2006.01)
  *A61M 16/20*  (2006.01)

(52) U.S. Cl.
  CPC .......... *A61M 16/10* (2013.01); *A61M 16/204* (2014.02); *B01D 53/0415* (2013.01); *B01D 53/0454* (2013.01); *C01B 13/02* (2013.01); *C01B 13/0259* (2013.01); *A61M 16/107* (2014.02); *A61M 2016/0027* (2013.01); *A61M 2016/0039* (2013.01); *A61M 2202/0208* (2013.01); *B01D 53/0446* (2013.01); *B01D 2253/108* (2013.01); *B01D 2256/12* (2013.01); *B01D 2257/102* (2013.01); *B01D 2259/40009* (2013.01); *B01D 2259/4533* (2013.01); *B01D 2259/4541* (2013.01)

(58) Field of Classification Search
  CPC .. A61M 2016/0027; A61M 2016/0039; C01B 13/02; C01B 13/0259; B01D 53/0454; B01D 53/0415; B01D 2257/102; B01D 2259/4533; B01D 2259/4541; B01D 2256/12; B01D 2253/108
  See application file for complete search history.

(56) References Cited

U.S. PATENT DOCUMENTS

| | | | |
|---|---|---|---|
| 4,681,099 A | 7/1987 | Sato | |
| 4,859,217 A | 8/1989 | Chao | |
| 5,531,807 A | 7/1996 | McCombs | |
| 6,520,176 B1 | 2/2003 | Dubois | |
| 6,532,960 B1 | 3/2003 | Yurko | |
| 6,729,327 B2 * | 5/2004 | McFarland, Jr. | A61M 11/02 128/203.12 |
| 6,764,534 B2 | 7/2004 | McCombs | |
| 7,368,005 B2 | 5/2008 | Bliss | |
| 7,402,193 B2 | 7/2008 | Bliss | |
| 7,794,522 B2 | 9/2010 | Bliss | |
| 7,837,761 B2 | 11/2010 | Bliss | |
| 2005/0103341 A1 | 5/2005 | Deane | |
| 2009/0145428 A1 * | 6/2009 | Sward | A61M 16/10 128/202.26 |

FOREIGN PATENT DOCUMENTS

| | | | |
|---|---|---|---|
| EP | 2186538 A2 | 5/2010 | |
| GB | 2380946 A | 4/2003 | |
| JP | 2002241110 A | 8/2002 | |
| JP | 2008036349 A | 2/2008 | |
| JP | 2008534233 A | 8/2008 | |
| JP | 2008295851 A | 12/2008 | |
| JP | 2009219990 A | 10/2009 | |
| JP | 2010240235 A | 10/2010 | |
| WO | WO2006108092 A1 | 10/2006 | |
| WO | WO 2007118055 A2 * | 10/2007 | ........... A61M 16/10 |
| WO | WO2013038297 A1 | 3/2013 | |
| WO | WO2013038299 A1 | 3/2013 | |

* cited by examiner

PROPORTIONAL OXYGEN CONSERVING DEVICE WITH FLOW SENSING

CROSS-REFERENCE TO RELATED APPLICATIONS

This patent application claims the priority benefit under 35 U.S.C. § 371 of international patent application No. PCT/IB2012/054643, filed Sep. 7, 2012, which claims the priority benefit under 35 U.S.C. § 119(e) of U.S. Provisional Application No. 61/533,871 filed on Sep. 13, 2011, the contents of which are herein incorporated by reference.

BACKGROUND OF THE INVENTION

1. Field of the Invention

The present disclosure pertains to a system and method for providing oxygen, and, in particular, a portable apparatus for concentrating oxygen by adsorption from air and methods for using such apparatus.

2. Description of the Related Art

Lung diseased patients often need supplemental oxygen to improve their comfort and/or quality of life. Stationary sources of oxygen are available, e.g., oxygen lines in hospitals or other facilities, that may provide oxygen to patients. To allow some mobility, cylinders of pure and/or concentrated oxygen can be provided that a patient may carry or otherwise take with them, e.g., on pull-along carts. Such cylinders, however, have limited volume and are large and heavy, limiting the patient's mobility.

Portable devices have been suggested that concentrate oxygen from ambient air to provide supplemental oxygen. For example, U.S. Pat. Nos. 5,531,807 6,520,176, 6,764,534, 7,368,005, 7,402,193, 7,794,522, and 7,837,761 disclose portable oxygen concentrators that separate nitrogen from ambient air, and deliver a stream of concentrated oxygen that may be stored in a tank or delivered directly to patients.

SUMMARY OF THE INVENTION

It is an object of one or more embodiments to provide a portable oxygen concentrator that includes a plurality of sieve beds configured to absorb nitrogen from air, each sieve bed comprising a first end port and a second end port; at least one reservoir, communicating with the second end ports of the plurality of sieve beds, configured to store oxygen-enriched gas exiting from the second end ports of the plurality of sieve beds; a compressor configured to deliver air at one or more desired pressures to the first end ports of the plurality of sieve beds; an oxygen delivery valve communicating with the reservoir via a delivery line; a flow sensor, associated with the delivery line, configured to measure a flow of the oxygen-enriched gas through the sensor and to output a signal indicative thereof; and a controller configured to control opening and closing the oxygen delivery valve to deliver the oxygen-enriched gas from the reservoir to a user based on the signal.

It is yet another aspect of one or more embodiments to provide a method for concentrating oxygen that includes providing a portable apparatus having a plurality of sieve beds, each sieve bed in the plurality of sieve beds including a first end and a second end, a reservoir storing oxygen-enriched gas exiting from the second ends of the plurality of sieve beds, a compressor, an oxygen delivery valve communicating with the reservoir via a delivery line, a flow sensor associated with the delivery line, and control electronics adapted to control operation of the oxygen delivery valve; measuring, via the flow sensor, a flow of the oxygen-enriched gas through the sensor and outputting a signal indicative thereof; and controlling, using the control electronics, the opening and closing the oxygen delivery valve to deliver the oxygen-enriched gas from the reservoir to a user based on the signal.

It is yet another aspect of one or more embodiments to provide a system configured to concentrate oxygen that includes compressing means for generating a supply of compressed air from a supply of air; separating means for providing a supply of oxygen-enriched gas from the supply of compressed air; oxygen storing means for storing the oxygen-enriched gas; valve means; sensing means for measuring a mass flow of the oxygen-enriched gas through the sensing means and for outputting a signal indicative thereof; and means for controlling opening and closing the valve means to deliver the oxygen-enriched gas to a user based on the signal.

These and other objects, features, and characteristics of the present embodiments, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
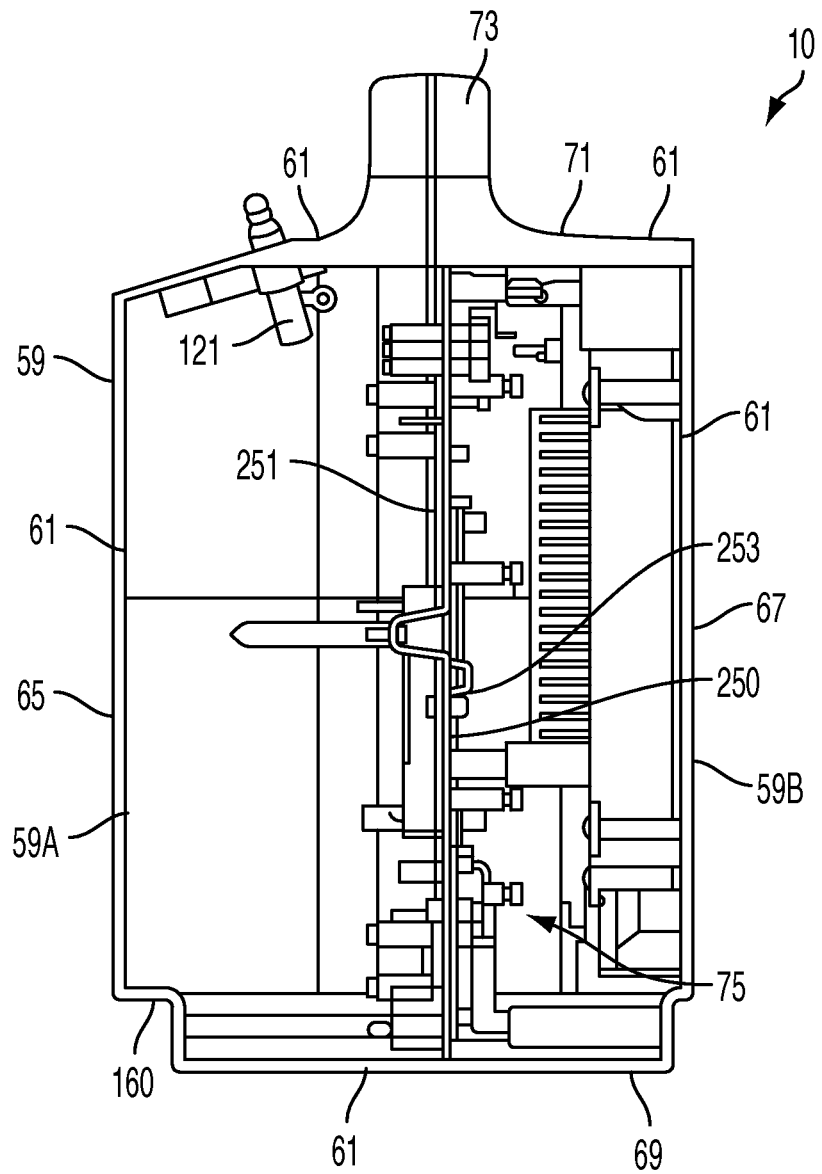
FIG. 1 is a side cross-sectional view of a portable oxygen concentrator (for sake of clarity compressor, air inlet filter, sieve beds, reservoir and controller are not shown) in accordance with an embodiment of the present disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIGS. 1-7 show an exemplary embodiment of a portable oxygen concentrator 10. Portable oxygen concentrator 10 includes a plurality of sieve beds (e.g., tanks or other beds) 12, a compressor 14, a reservoir 18 (e.g., an oxygen storage tank), an oxygen delivery valve 19 communicating with oxygen storage tank or reservoir 18 via a delivery line 21, a flow sensor 23 associated with delivery line 21 and configured to measure a flow of the oxygen-enriched gas through flow sensor 23 and output a signal indicative thereof, and a controller 22 configured to control opening and closing oxygen delivery valve 19 to deliver the oxygen-enriched gas from reservoir 18 to a user based on the signal.

Optionally, portable oxygen concentrator 10 may include one or more additional components, e.g., one or more check valves, filters, sensors, electrical power sources (not shown), and/or other components, at least some of which may be coupled to controller 22 (and/or one or more additional controllers, also not shown), as described further below. It will be appreciated that the terms "airflow," "air," or "gas" may be used generically herein, even though the particular fluid involved may be ambient air, pressurized nitrogen, concentrated oxygen, and the like.

Figure 4:
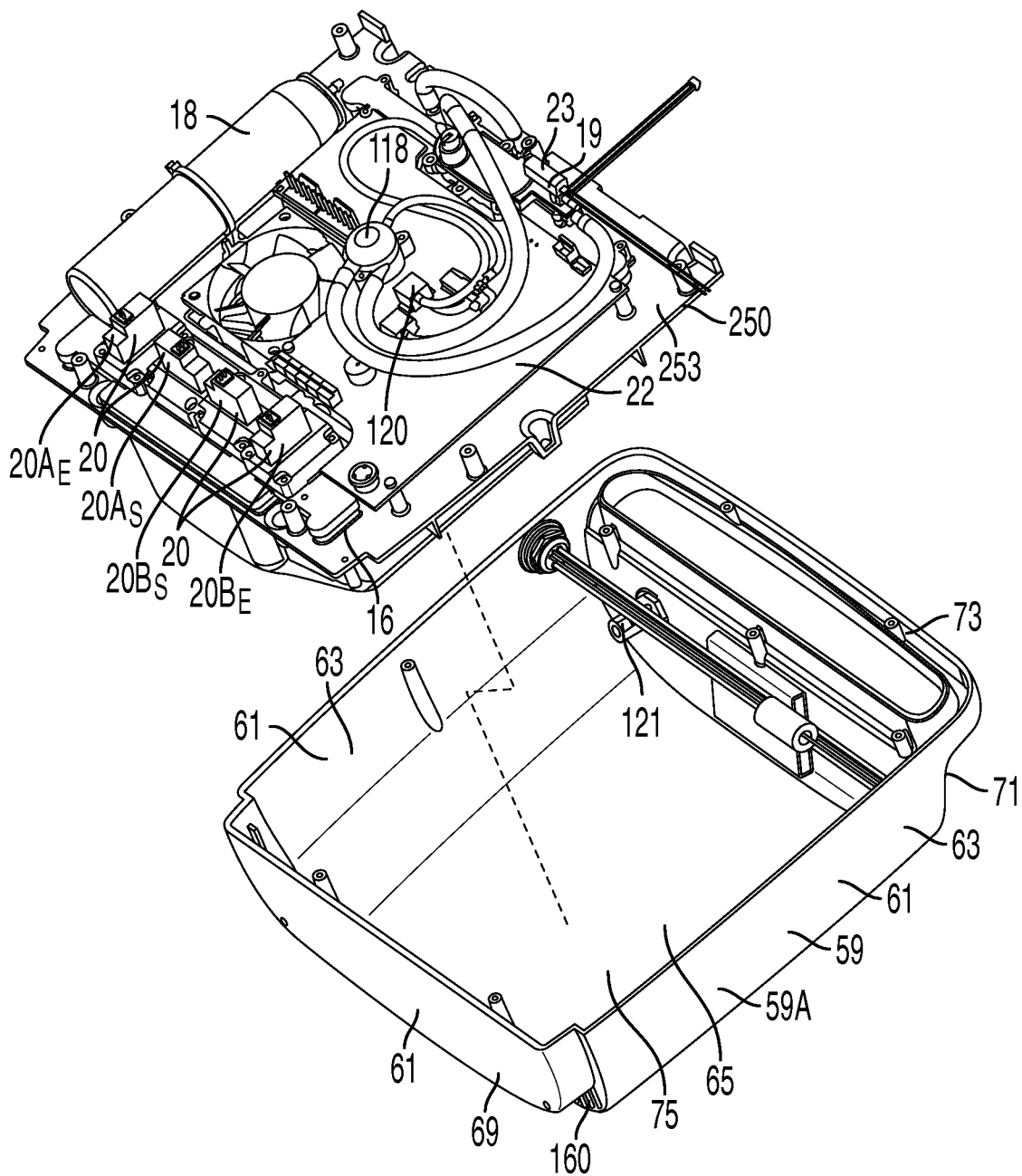
FIG. 4 is a perspective view of a housing member of the portable oxygen concentrator and one side of the support member with reservoir, valves, and controller disposed thereon in accordance with an embodiment of the present disclosure.
Figure 5:
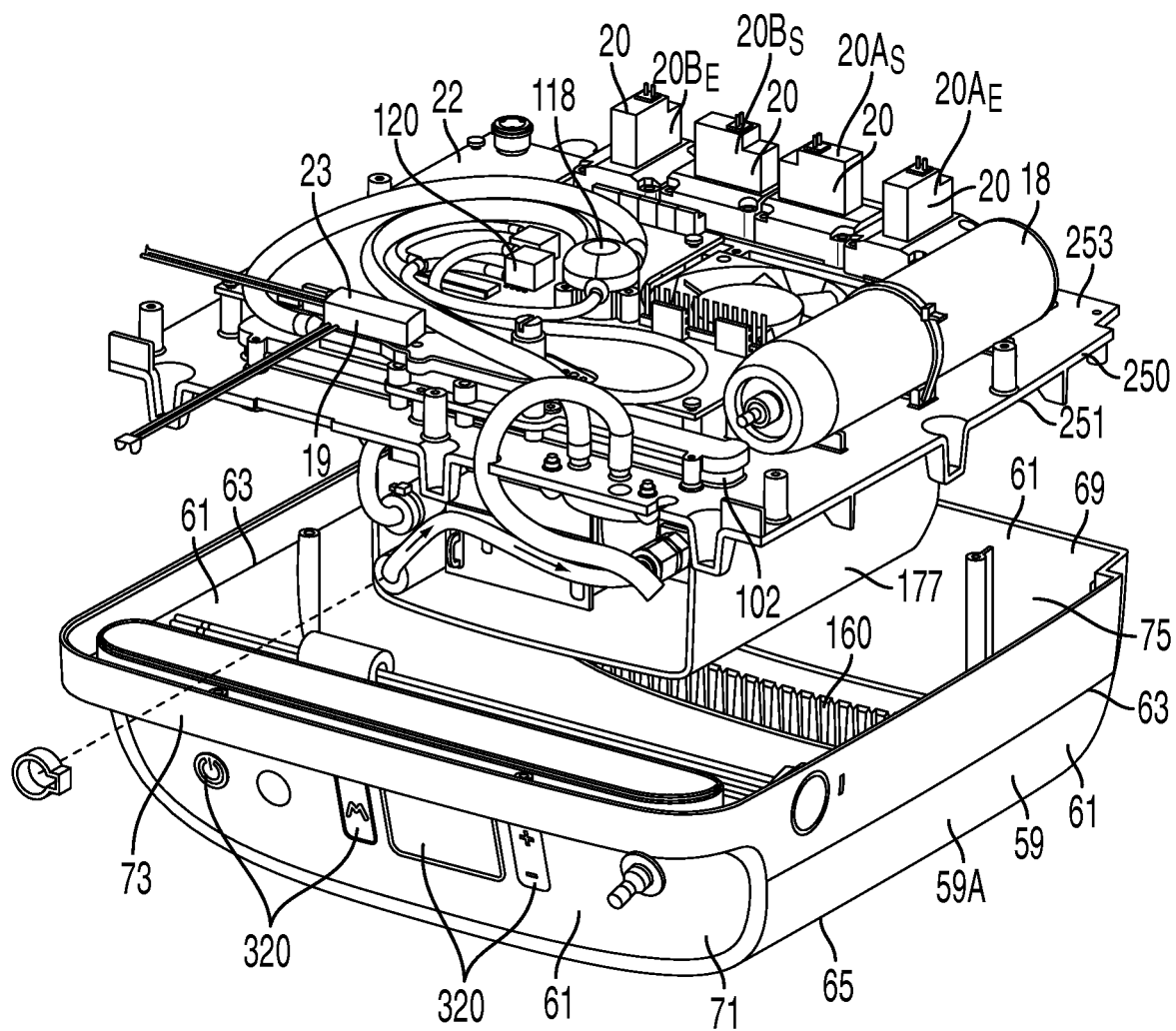
FIG. 5 is another perspective view of the housing member and the support member of the portable oxygen concentrator in accordance with an embodiment of the present disclosure.

Referring to FIGS. 1, 4 and 5, portable oxygen concentrator 10 may include a housing 59 comprising a plurality of walls 61 that may define outer structural surface of portable oxygen concentrator 10. Plurality of walls 61 may include a pair of side walls 63, a front wall 65, a top wall 71, a bottom wall 69, and a rear wall 67. Portable oxygen concentrator 10 may include a carrying handle 73 connected to at least one of walls 61 (e.g., top wall 71) to enable portable oxygen concentrator 10 to be transported.

In one embodiment, housing 59 may be formed of at least two mating housing members 59A and 59B cooperating with each other to define a hollow interior 75 therein. Hollow interior 75 of housing 59 includes a support member 250, sieve beds 12, reservoir 18, compressor 14 and other components of portable oxygen concentrator 10. First mating housing member 59A includes front wall 65, and at least a portion of side walls 63, bottom wall 69, top wall 71, and handle 73, while second mating member 59B includes rear wall 67, and at least a portion of side walls 63, bottom wall 69, top wall 71, and handle 73. First mating housing member 59A and the second mating housing member 59B may be connected to each other using any known attachment mechanism, for example, using fasteners.

In one embodiment, side walls 63 and/or bottom wall 69 may include one or more inlet openings 160 (FIGS. 4 and 5) that may communicate with hollow interior 75 of portable oxygen concentrator 10. Inlet openings 160 are configured to allow air to pass easily through inlet openings 160, yet preventing large objects from passing therethrough.

Figure 3:
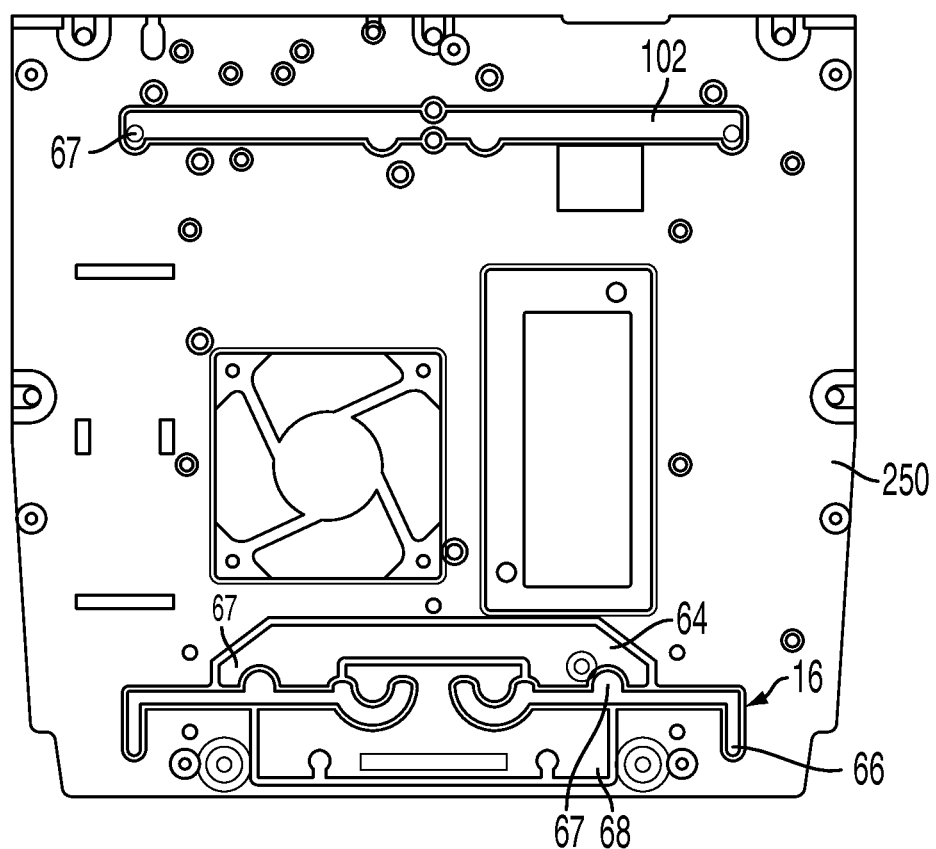
FIG. 3 is a rear view of a support member (or a central chassis) of the portable oxygen concentrator with integrally formed upper (oxygen) and lower (air) manifolds in accordance with an embodiment of the present disclosure.

As shown in FIGS. 1 and 3, portable oxygen concentrator 10 may include a support member 250. The support member 250 may form a central chassis or spine for portable oxygen concentrator 10. An air manifold 16 and an oxygen delivery manifold 102 of portable oxygen concentrator 10 are integrally formed or integrally molded on support member 250. Additional information on an exemplary central chassis or spine with integrally formed air manifold 16 and oxygen delivery manifold 102 may be found in U.S. provisional patent application No. 61/533,962, filed Sep. 13, 2011, the entire disclosure of which is expressly incorporated by reference herein.

As will be described below, air manifold 16 includes inlet air passages 64-66 for air to enter sieve beds 12 and includes an exit passage 68 for nitrogen to be exhausted out of sieve beds 12 into the atmosphere. Oxygen delivery manifold 102 includes a pathways 108-109 for oxygen-enriched gas from a second end ports 34 of sieve beds 12 to reservoir 18. Oxygen delivery manifold 102 also includes pathways 108 and 109 for oxygen-enriched gas from reservoir 18 to a device (not shown) for delivering the oxygen to a user.

Figure 2:
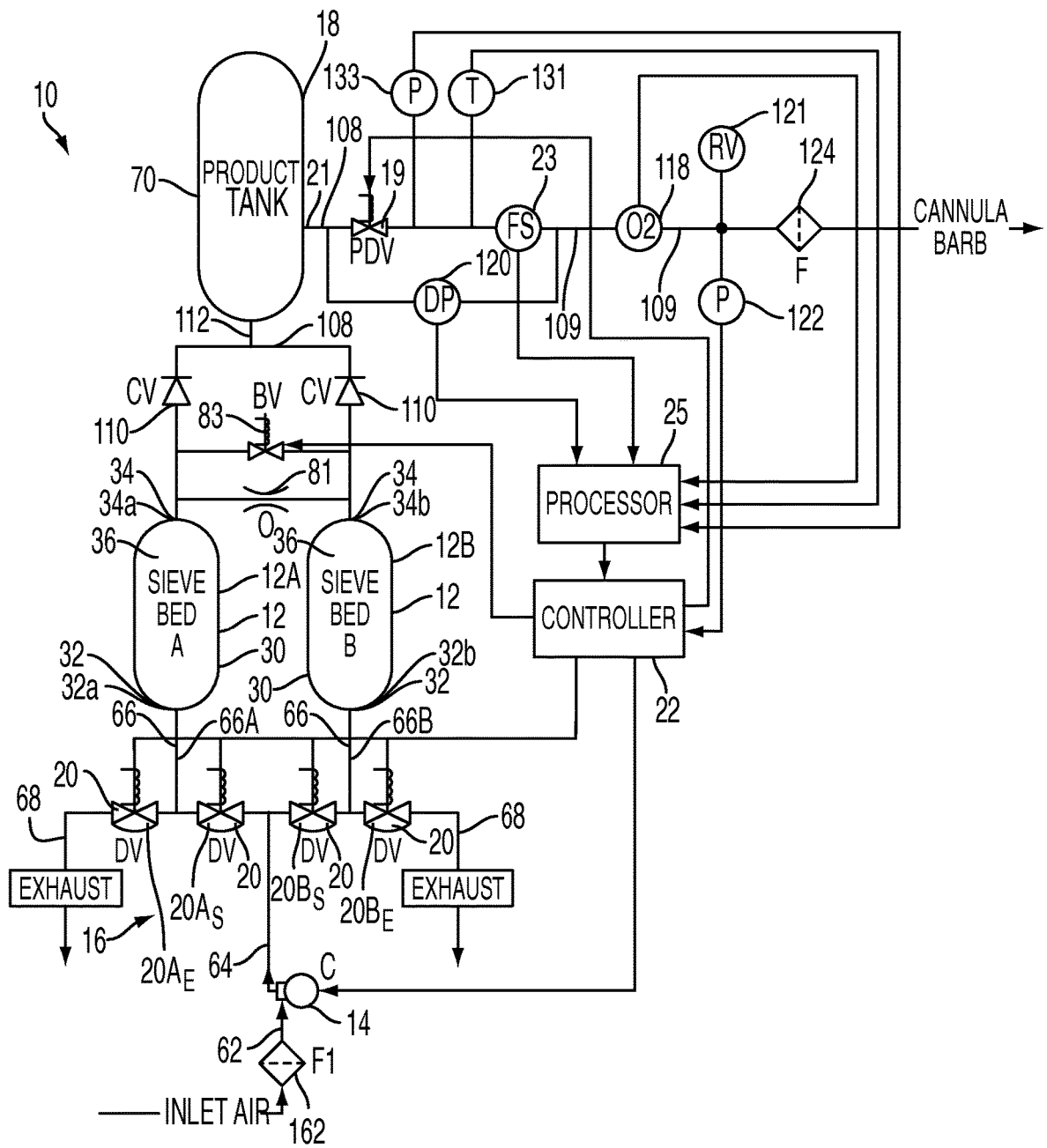
FIG. 2 schematically illustrates the portable oxygen concentrator in accordance with an embodiment of the present disclosure.

As shown in FIGS. 2 and 3, air manifold 16 defines a plurality of passages 64-68 therein. A base of the air manifold 16 may include channels 67 that at least partially define a compressor outlet passage 64, sieve bed 12, passage 66, and an exit passage 68.

Optionally, an inlet air filter 162 (FIGS. 2 and 6) may be provided to remove dust or other particles from the ambient air drawn into inlet openings 160 (FIGS. 4 and 5) before it enters compressor 14.

Compressor 14 may be any device capable of drawing ambient air into portable oxygen concentrator 10 and compressing the air to one or more desired pressures for delivery to sieve beds 12. In one embodiment, compressor 14 is a multiple headed device that includes a motor, a cam assembly coupled to the motor, drive shafts or rods coupled to the cam assembly, and a plurality of diaphragm assemblies or heads coupled to the drive shafts. Additional information on an exemplary compressor that may be included in portable oxygen concentrator 10 may be found in U.S. Pat. No. 7,794,522, the entire disclosure of which is expressly incorporated by reference herein.

Figure 6:
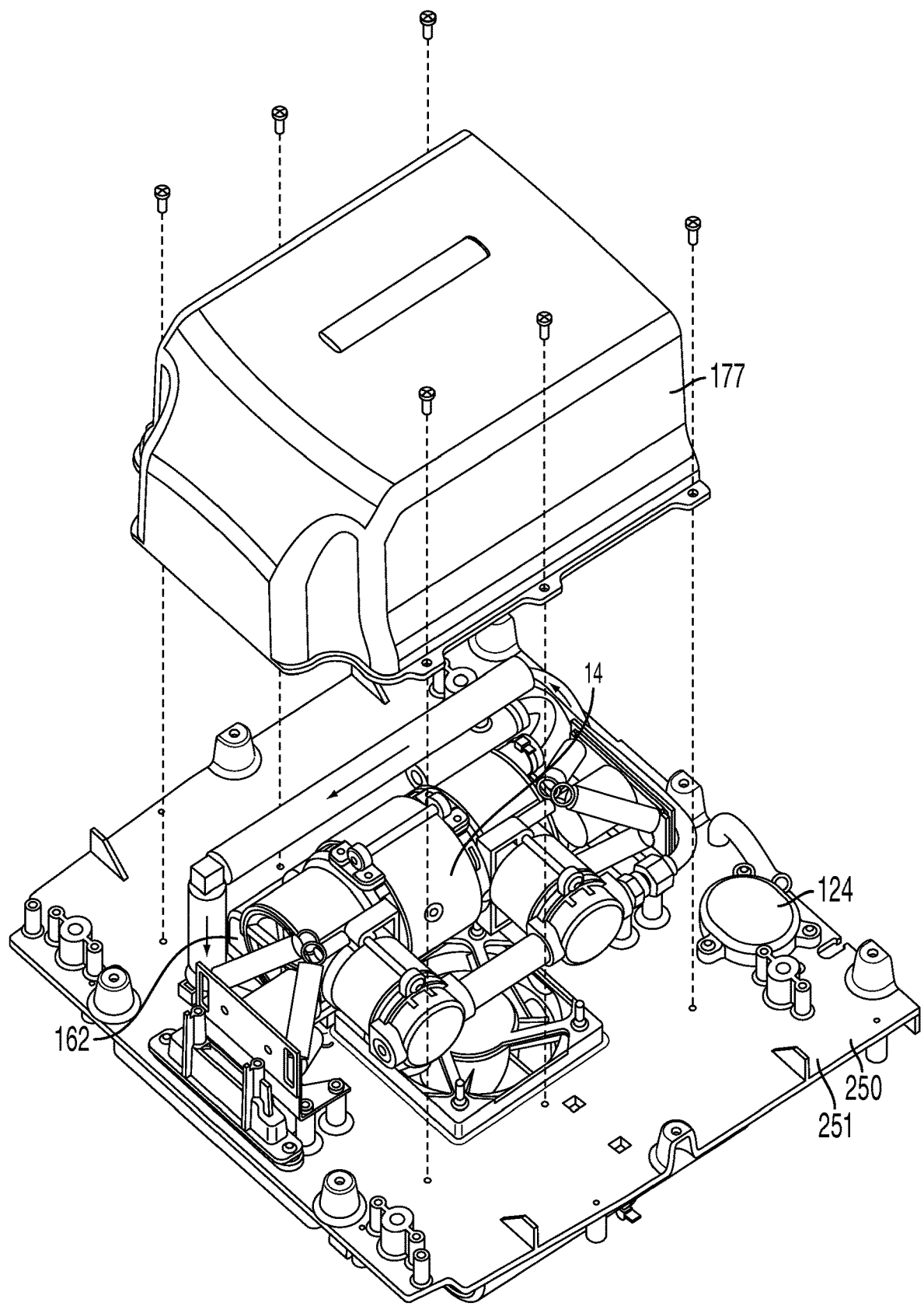
FIG. 6 is a perspective view of the support member with compressor, air filters, and sound shield member attached on the other side of the support member in accordance with an embodiment of the present disclosure.

In order to reduce the noise level of compressor 14, a sound shield 177 (as shown in FIG. 6) may be formed around compressor 14 to absorb noise generated by the compressor 14. As shown in FIG. 6, compressor 14, inlet air filter 162 and sound shield 177 are positioned on a first side surface 251 of support member 250.

Referring to FIGS. 2, 4 and 5, portable oxygen concentrator 10 may include a set of an air control valves 20 for creating one or more flow paths through passages 64-68 within air manifold 16. Controller 22 may be coupled to air control valves 20 for selectively opening and closing air control valves 20 to control airflow through air manifold 16. That is, air control valves 20 may be selectively opened and closed to provide flow paths, e.g., from a compressor outlet passage 64 to sieve bed 12, passage 66 and/or from sieve bed 12, passage 66 to exit passage 68. For example, when a supply air control valve $20A_S$ is open, a flow path may defined from compressor 14, through compressor outlet passage 64 and a supply air control valve 20A$_S$, into a sieve bed 12A. When exhaust an air control valve 20B$_E$ is open, a flow path may be defined from a sieve bed 12B, through a sieve bed passage 66B and an air control valve 20B$_E$, and into exhaust passage 68.

Figure 7:
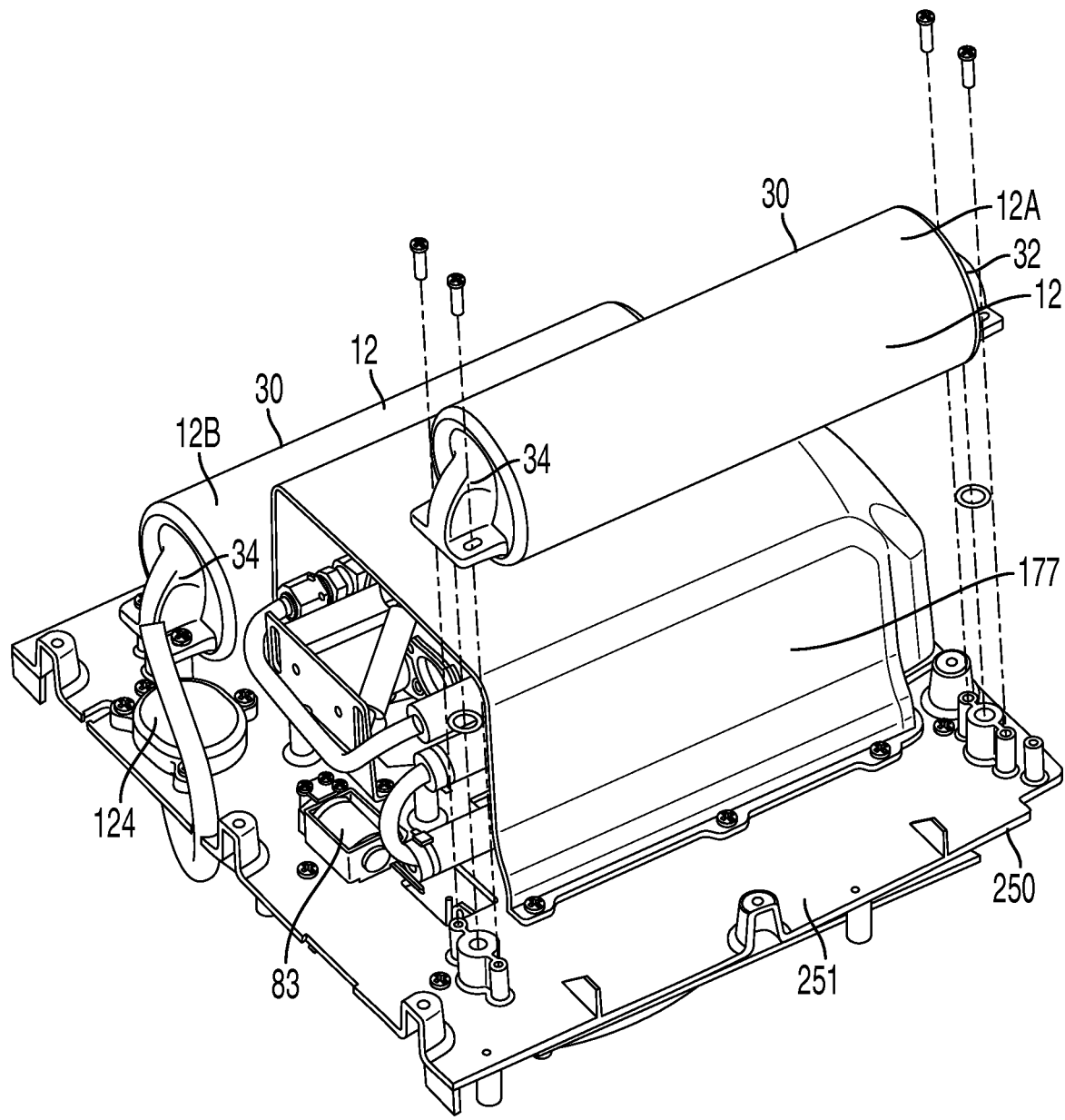
FIG. 7 is another perspective view of (the same side as shown in FIG. 6) of the support member with sieve beds attached thereon in accordance with an embodiment of the present disclosure.

Referring to FIGS. 2 and 7, sieve beds 12 are configured to absorb nitrogen from air. Each sieve bed 12 includes an outer casing 30, e.g., in the shape of an elongate hollow cylinder, including a first end port 32 and a second end port 34. Outer casing 30 may be formed from substantially rigid material, e.g., plastic, such as acrylonitrile butadiene styrene ("ABS"), polycarbonate, and the like, metal, such as aluminum, or composite materials. Outer casing 30 may have any desired shape that may depend upon spatial, performance, and/or structural criteria. For example, outer casing 30 may have a round cylindrical shape, an elliptical, square, rectangular, or other regular or irregular polygonal shaped cross-section.

Outer casing 30 may be at least partially filled with filtration media or a sieve material 36 to provide sieve beds 12 capable of adsorbing nitrogen from air delivered into sieve beds 12 under pressure. To hold sieve material 36 within casing 30, sieve beds 12 may include discs or plates (not shown) adjacent to each of first end port 32 and second end port 34 of casing 30. The plates may be spaced apart from one another to define a desired volume between the plates and within casing 30. The plates may include one or more openings or pores (not shown) therethrough to allow airflow through the plates. Generally, sieve beds 12 may be filled such that there are no substantial voids in sieve material 36, e.g., such that sieve material 36 is substantially packed between the plates. Additional information on exemplary plates that may be included in portable oxygen concentrator 10 may be found in U.S. Pat. No. 7,794,522, the entire disclosure of which is expressly incorporated by reference herein.

Sieve material 36 may include one or more known materials capable of adsorbing nitrogen from pressurized ambient air, thereby allowing oxygen to be bled off or otherwise evacuated from sieve beds 12. Exemplary sieve materials that may be used include synthetic zeolite, LiX, and the like, such as UOP Oxysiv 5, 5A, Oxysiv MDX, or Zeochem Z10-06. It may be desirable to provide multiple layers of sieve material 36 within sieve beds 12, e.g., providing sieve material with different properties in layers between first end port 32 and second end port 34.

Although two sieve beds 12 are shown in FIGS. 2 and 7, it will be appreciated that one or more sieve beds 12 may be provided, e.g., depending upon the desired weight, performance efficiency, and the like. Additional information on exemplary sieve beds and/or sieve materials that may be included in portable oxygen concentrator 10 may be found in U.S. Pat. Nos. 4,859,217 and 7,794,522, the entire disclosures of which are expressly incorporated by reference herein.

Referring to FIG. 2, portable oxygen concentrator 10 may include a purge orifice 81, which may provide a passage communicating directly between second end ports 34 of sieve beds 12. Purge orifice 81 may remain continuously open, thereby providing a passage for oxygen to pass from one sieve bed 12 to the other, e.g., while the one sieve bed 12 is charging and the other is purging. Additional information on an exemplary purge orifice 81 that may be included in portable oxygen concentrator 10 may be found in U.S. Pat. No. 7,794,522, the entire disclosure of which is expressly incorporated by reference herein.

Referring to FIGS. 2 and 7, portable oxygen concentrator 10 may include an oxygen side balance valve 83. Oxygen side balance valve 83 is configured to balance bed pressures in sieve bed 12A and sieve bed 12B. During the pressure cycling of sieve beds 12, the pressure in sieve bed 12A may be higher than the pressure in sieve bed 12B indicating that the beds are not balanced. In such an instance, oxygen side balance valve 83 is operated (opened) to relieve some pressure from sieve bed 12A and provide the pressure to sieve bed 12B, for example, before compressor 14 switches from sieve bed 12A to sieve bed 12B to supply compressed air to sieve bed 12B. Transferring some pressure from sieve bed 12A to sieve bed 12B allows sieve bed 12B be at some intermediate pressure (rather than be at a zero pressure), when compressor starts supplying compressed air to sieve bed 12B. Since oxygen side balance valve 83 allows sieve bed 12B be at some intermediate pressure (rather than be at a zero pressure), oxygen side balance valve 83 maximizes efficiency, e.g., to reduce power consumption of portable oxygen concentrator 10.

Referring to FIG. 2, portable oxygen concentrator 10 may include a pair of check valves 110. Check valves 110 may simply be pressure-activated valves. Check valves 110 may simply be spring biased valves that open in one direction depending upon the pressure differential across the valve, such as conventional umbrella-type valves. When oxygen delivery manifold 102 is mounted to or adjacent sieve beds 12 and reservoir 18, check valves 110 provide one-way flow paths from sieve beds 12 into an oxygen delivery passage 108. Oxygen delivery passage 108 communicates directly and continuously with reservoir 18 via an opening 112.

Referring to FIGS. 2, 4 and 5, reservoir 18 is in communication with second end ports 34 of sieve beds 12. Reservoir 18 may include an elongate tubular casing for storing oxygen-enriched gas exiting from second end ports 34 of sieve beds 12. The casing of reservoir 18 may be formed from plastic, such as ABS, polycarbonate, and the like, metal, such as aluminum, or composite materials, similar to the other components of portable oxygen concentrator 10 described herein.

In a further alternative, portable oxygen concentrator 10 may include multiple reservoirs 18 (not shown) that may be provided at one or more locations within portable oxygen concentrator 10, e.g., placed in different locations where space is available, yet minimizing the overall size of portable oxygen concentrator 10. The reservoirs 18 may be connected to one another via one or more flexible tubes (not shown) and/or via oxygen delivery manifold 102 to allow oxygen to be delivered to and withdrawn from the reservoirs. Optionally, in this alternative, one or more valves may be provided for controlling flow of oxygen into and out of the reservoirs.

In addition or alternatively, portable oxygen concentrator 10 may include one or more flexible reservoirs 18, e.g., bags or other containers that may expand or contract as oxygen is delivered into or out of them. Reservoirs 18 may have predetermined shapes as they expand or may expand elastically to fill available space within portable oxygen concentrator 10. Optionally, one or more rigid reservoirs may be provided that communicate with one or more flexible reservoirs (not shown), e.g., to conserve space within portable oxygen concentrator 10. In further alternatives, one or more reservoirs 18 may be provided as portions of one or both of air manifold 16 and oxygen delivery manifold 102, rather than as a separate component.

Referring to FIG. 2, oxygen delivery manifold 102 may be provided for delivering oxygen from sieve beds 12, to reservoir 18 and then to a user of portable oxygen concentrator 10. Oxygen delivery manifold 102 includes one or more oxygen delivery passages 108109 for communicating with components related to delivering oxygen to a user of portable oxygen concentrator 10.

Air manifold 16 and oxygen delivery manifold 102 may be formed from any engineering grade material, e.g., plastic, such as ABS, polycarbonate, and the like; metal, such as aluminum, and the like; or composite materials. As noted above, air manifold 16 and oxygen delivery manifold 102 may be formed by integrally formed in support member 250. Air manifold 16 and oxygen delivery manifold 102 may be formed by injection molding, casting, machining, and the like. In one embodiment, air manifold 16 and oxygen delivery manifold 102 may be formed from relatively lightweight plastic material.

Referring to FIGS. 2, 4 and 5, oxygen delivery valve 19 may be a proportional valve that is communicating with reservoir 18 via delivery line 21. Controller 22 receives inputs from sensors, including but not limited to a pressure sensors 120 or 122, an oxygen sensor 118 and/or flow sensor 23. Controller 22 is configured to control when proportional (patient delivery) oxygen delivery valve 19 is fully open, fully closed, or partially open as well as the degree to which oxygen delivery valve 19 is open based on the received inputs from the sensors.

In one embodiment, oxygen delivery valve 19 is an adjustable restriction. For example, oxygen delivery valve 19 is a piezo-electric valve, such as a piezo-electric valve manufactured by Festo (Part or Model Number: VEMR-B-6-13-D6-W4-22X5-R5). The piezo-electric valve generally consumes low-power thereby extending the battery life of portable oxygen concentrator 10.

Referring to FIG. 2, flow sensor 23 is associated with delivery line 21 and is configured to measure the instantaneous mass flow of the oxygen passing through delivery line 21 and to provide feed-back to proportional delivery oxygen delivery valve 19. In one embodiment, flow sensor 23 is a mass flow sensor, such as a flow sensor manufactured by Honeywell (Part or Model Number: AWM 92100V) or a flow sensor manufactured by Festo (Part or Model Number 1238841). Referring to FIG. 2, portable oxygen concentrator 10 includes an oxygen gas temperature sensor 131, such as a thermistor, a thermocouple, or any other temperature sensor and a local pressure sensor 133, such as those made by a barometric pressure sensor manufactured by Freescale (Part or Model Number: MPXM2102A). Oxygen gas temperature sensor 131 is configured to measure the temperature of the oxygen passing through delivery line 21, while local pressure sensor 133 is configured to measure the local ambient pressure.

The measured oxygen temperature and the measured local ambient pressure are sent to a processor 25. Processor 25 is configured to use this oxygen temperature measurement from oxygen gas temperature sensor 131 and the local ambient pressure measurement from local pressure sensor 133 along with the mass flow rate measurement obtained from flow sensor 23 to obtain a volumetric flow rate measurement.

In the illustrated embodiment, as shown in FIG. 4, oxygen gas temperature sensor 131 and local pressure sensor 133 are positioned upstream of flow sensor 23. In another embodiment, oxygen gas temperature sensor 131 and local pressure sensor 133 are positioned downstream (still in the vicinity) of flow sensor 23.

Referring to FIGS. 2, 4 and 5, pressure sensor 120 (e.g., a differential pressure sensor) may also be mounted to and/or below the oxygen delivery manifold 102 such that ports of pressure sensor 120 may measure a pressure difference between oxygen delivery passages 108-109, and consequently across oxygen delivery valve 19. Optionally, pressure sensor 120 may be used to obtain reservoir pressure. For example, when oxygen delivery valve 19 is closed, pressure upstream of oxygen delivery valve 19 may correspond substantially to the pressure within reservoir 18.

As shown in FIG. 2, pressure sensor 120 may be coupled to processor 25, e.g., to provide signals that may be processed by processor 25 to determine the pressure differential across oxygen delivery valve 19. Controller 22 may use this pressure differential to determine a flow rate of the oxygen being delivered from portable oxygen concentrator 10 or other parameters of oxygen being delivered. Controller 22 may change the frequency and/or duration that oxygen delivery valve 19 is open based upon the resulting flow rates, e.g., based upon one or more feedback parameters.

Referring to FIGS. 2, 4 and 5, oxygen sensor 118 may also be mounted to and/or below oxygen delivery manifold 102. Oxygen sensor 118 may be capable of measuring the purity of oxygen passing therethrough, e.g., an ultrasonic sensor that measures the speed of sound of the gas passing through oxygen sensor 118, such as those made by Douglas Scientific of Shawnee, Kans. Alternatively, oxygen sensor 118 may be a ceramic or sidestream sensor.

Oxygen sensor 118 may be coupled to processor 25 and may generate electrical signals proportional to the purity that may be processed by processor 25 and used by controller 22 to change operation of portable oxygen concentrator 10. Because the accuracy of oxygen sensor 118 may be affected by airflow therethrough, it may be desirable to sample the purity signals during no flow conditions, e.g., when oxygen delivery valve 19 is closed.

Pressure sensor 122 may be coupled to oxygen delivery manifold 102. Pressure sensor 122 may be a piezo resistive pressure sensor capable of measuring absolute pressure. Pressure sensor 122 provides a pressure reading that may be used to detect when a user is beginning to inhale. Exemplary transducers that may be used include the Honeywell Microswitch 24PC01SMT Transducer, the Sensym SX01, Motorola MOX, or others made by All Sensors. Because pressure sensor 122 may be exposed to the full system pressure of portable oxygen concentrator 10, it may be desirable for the overpressure rating of pressure sensor 122 to exceed the full system pressure. Pressure sensor 122 may be coupled to processor 25 for providing signals proportional to the pressure detected by pressure sensor 122. Additional information on an exemplary pressure sensor that may be included in portable oxygen concentrator 10 may be found in U.S. Pat. No. 7,794,522, the entire disclosure of which is expressly incorporated by reference herein.

As shown in FIGS. 4 and 5, reservoir 18, controller 22 (with various sensors on it), air control valves 20, air manifold 16 and oxygen delivery manifold 102 are located on side 253 of support member 250.

Oxygen delivered from oxygen sensor 118 may then pass through an air filter 124 and be delivered to the user. Air filter 124 may be mounted to or adjacent oxygen delivery manifold 102, and may include any conventional filter media for removing undesired particles from oxygen being delivered to the user. As shown in FIGS. 6 and 7, air filter 124 is located on a first side surface 251 of support member 250.

It will be appreciated that other configurations and/or components may be provided for delivering oxygen to the user, rather than oxygen delivery manifold 102 and the components attached thereto described above. In addition, although the components, e.g., oxygen delivery valve 19, pressure sensors 120, 122, 133, flow sensor 23, oxygen sensor 118, oxygen gas temperature sensor 131 and air filter 124 are described in a particular sequence (relative to oxygen flowing through oxygen delivery manifold 102), the sequence of these components may be changed, if desired.

Controller 22 may include one or more hardware components and/or software modules that control one or more aspects of the operation of portable oxygen concentrator 10. Controller 22 may be coupled to one or more components of portable oxygen concentrator 10, e.g., compressor 14, air control valves 20, and/or oxygen delivery valve 19. Controller 22 may also be coupled to one or more sensing components of portable oxygen concentrator 10, e.g., pressure sensors 120, 122, oxygen gas temperature sensor 131, local pressure sensor 133, flow sensor 23 and/or oxygen sensor 118 via processor 25. The components may be coupled by one or more wires or other electrical leads capable of receiving and/or transmitting signals between controller 22 and the components.

Controller 22 may also be coupled to a user interface 320 (FIG. 5), which may include one or more displays and/or input devices. User interface 320 may be a touch-screen display that may be mounted to portable oxygen concentrator 10. User interface 320 may display information regarding parameters related to the operation of portable oxygen concentrator 10 and/or allow the user to change the parameters, e.g., turn portable oxygen concentrator 10 on and off, change dose setting or desired flow rate, etc. Portable oxygen concentrator 10 may include multiple displays and/or input devices, e.g., on/off switches, dials, buttons, and the like (not shown). User interface 320 may be coupled to controller 22 by one or more wires and/or other electrical leads (not shown for simplicity), similar to the other components.

Controller 22 may include a single electrical circuit board that includes a plurality of electrical components thereon. These components may include one or more processors, memory, switches, fans, battery chargers, and the like (not shown) mounted to the circuit board. It will be appreciated that controller 22 may be provided as multiple subcontrollers that control different aspects of the operation of portable oxygen concentrator 10. For example, a first subcontroller may control operation of compressor 14 and the sequence of opening and closing of air control valves 20, e.g., to charge and purge sieve beds 12 in a desired manner Additional information on an exemplary first subcontroller that may be included in portable oxygen concentrator 10 may be found in U.S. Pat. No. 7,794,522, the entire disclosure of which is expressly incorporated by reference herein.

A second subcontroller may control operation of oxygen delivery valve 19, e.g., to deliver oxygen from reservoir 18 to a user based upon signals received from pressure sensor 120, from flow sensor 23, from oxygen gas temperature sensor 131 and from local pressure sensor 133. The second subcontroller may also receive input instructions from the user and/or display information on user interface 320. In addition, the subcontrollers or other components of controller 22 may share information in a desired manner, as described below. Thus, controller 22 may include one or more components, whose functionality may be interchanged with other components, and controller 22 should not be limited to the specific examples described herein.

Portable oxygen concentrator 10 may include one or more power sources, coupled to controller 22, processor 25, compressor 14, air control valves 20, and/or oxygen delivery valve 19. For example, a pair of batteries may be provided that may be mounted or otherwise secured to portable oxygen concentrator 10. Mounts, straps or supports (not shown) may be used to secure the batteries to portable oxygen concentrator 10. Additional information on exemplary batteries that may be included in portable oxygen concentrator 10 may be found in U.S. Pat. No. 7,794,522, the entire disclosure of which is expressly incorporated by reference herein.

Controller 22 may control distribution of power from a batteries 148 to other components within portable oxygen concentrator 10. For example, controller 22 may draw power from one of the batteries 148 until its power is reduced to a predetermined level, whereupon controller 22 may automatically switch to the other of the batteries.

Optionally, portable oxygen concentrator 10 may include an adapter such that an external power source, e.g., a conventional AC power source, such as a wall outlet, or a portable AC or DC power source, such as an automotive lighter outlet, a solar panel device, and the like (not shown). Any transformers or other components (also not shown) necessary to convert such external electrical energy such that it may be used by portable oxygen concentrator 10 may be provided within portable oxygen concentrator 10, in the cables connecting portable oxygen concentrator 10 to the external power source, or in the external device itself.

Optionally, controller 22 may direct some electrical energy from external sources back to batteries 148 to recharge them in a conventional manner. Controller 22 may also display the status of the electrical energy of portable oxygen concentrator 10, e.g., automatically or upon being prompted via user interface 320, such as the power level of the batteries, whether portable oxygen concentrator 10 is connected to an external power source, and the like. Controller 22 may include one or more dedicated components for performing one or more of these functions. An exemplary battery management integrated circuit that may be included in controller 22 of portable oxygen concentrator 10 may be found in U.S. Pat. No. 7,794,522, the entire disclosure of which is expressly incorporated by reference herein.

Processor 25 of portable oxygen concentrator 10 may be configured to receive the signals from one or more sensing components of portable oxygen concentrator 10, e.g., flow sensor 23, oxygen gas temperature sensor 131, local pressure sensor 133 and/or pressure sensor 120 to determine a flow of the oxygen-enriched gas in the delivery line over a predetermined period of time, a volume of the oxygen-enriched gas in the delivery line over a predetermined period of time or both based on the received signal.

Portable oxygen concentrator 10 may also include a dynamic noise control that is configured to dynamically change an inlet port size or shape of the inlet air filter 162 proportionately for all input/output settings. For example, the higher the volume of air needed the larger the input port size and vice versa. An exemplary dynamic noise control that may be included in portable oxygen concentrator 10 may be found in U.S. provisional patent application No. 61/533,864, filed Sep. 13, 2011, the entire disclosure of which is expressly incorporated by reference herein.

Portable oxygen concentrator 10 may also include an overpressure relief valve 121 pneumatically coupled into delivery line 21 to serve as a protection device for pressure sensor 122. Overpressure relief valve 121 allows for the use of a single supply or delivery line to be used for both pulse and continuous flow delivery from portable oxygen concentrator 10. Overpressure relief valve 121 may be set to a level below an operational proof pressure of pressure sensor 122.

If the supply circuit attempts to exceed this proof pressure, due to kinked tubing or otherwise, overpressure relief valve 121 is configured to open and maintain the pressure in the delivery circuit below a level at which pressure sensor 122 would be damaged. Exemplary overpressure relief valve 121 that may be included in portable oxygen concentrator 10 may be found in U.S. provisional patent application No. 61/533,912, filed Sep. 13, 2011, the entire disclosure of which is expressly incorporated by reference herein.

The basic operation of portable oxygen concentrator 10 will now be described. Generally, operation of portable oxygen concentrator 10 has two aspects, concentrating oxygen from ambient air by adsorption within sieve beds 12, and delivering concentrated oxygen to a user from reservoir 18. Each aspect of portable oxygen concentrator 10 may operate independently of the other, or they may be interrelated, e.g., based upon one or more related parameters.

Portable oxygen concentrator 10 may be operated using one or more optional methods, such as those described below, to increase efficiency or other performance characteristics of portable oxygen concentrator 10. For example, based upon measurements of pressure and/or flow sensors, the operating conditions of portable oxygen concentrator 10 may be adjusted to increase output flow rate and/or pressure, reduce power consumption, and the like.

The aspect of concentrating oxygen from ambient air by adsorption within sieve beds 12 is explained in great detail in U.S. Pat. No. 7,794,522, the entire disclosure of which is expressly incorporated by reference herein. With concentrated oxygen stored in reservoir 18, portable oxygen concentrator 10 may be used to deliver concentrated oxygen to a user. As described above, controller 22 may be coupled to oxygen delivery valve 19 for opening and closing oxygen delivery valve 19 to deliver oxygen from reservoir 18 to a user of portable oxygen concentrator 10.

In one embodiment, controller 22 may periodically open oxygen delivery valve 19 for predetermined "pulses." During pulse delivery, a "bolus" of oxygen is delivered to the user, i.e., oxygen delivery valve 19 is opened for a predetermined pulse duration, and thereafter closed until the next bolus is to be delivered. Alternatively, controller 22 may open oxygen delivery valve 19 for continuous delivery, e.g., throttling oxygen delivery valve 19 to adjust the flow rate to the user. In a further alternative, controller 22 may periodically open and throttle oxygen delivery valve 19 for a predetermined time to vary the volume of the bolus delivered.

Flow sensor 23 may be used to monitor flow of the oxygen-enriched gas flowing through flow sensor 23 and to provide a feed-back signal to controller 22. The signal from flow sensor 23 is used to control opening and closing oxygen delivery valve 19 to deliver the oxygen-enriched gas from reservoir 18 to a user, when portable oxygen concentrator 10 is operating to supply a continuous flow of oxygen.

Pressure sensor 120 may be used to monitor flow of the oxygen-enriched gas flowing through pressure sensor 120 and to provide a feed-back pressure differential signal to controller 22. The pressure differential signal from pressure sensor 120 is used to control opening and closing oxygen delivery valve 19 to deliver the oxygen-enriched gas from reservoir 18 to a user, when portable oxygen concentrator 10 is operating in pulse delivery where oxygen is supplied in predetermined pulses.

Controller 22 may have a predetermined or a set target flow rate stored in memory. The target flow rate may be provided and may be changed by the user using user interface 320. The target flow rate may be a volume flow rate in units of liter per minute (LPM). For example, portable oxygen concentrator 10 may provide a 1.5 Liter per minute (LPM), a 2 LPM, a 2.5 LPM, or a 3 LPM.

If the measured flow rate is below the target flow rate, controller 22 controls the oxygen delivery valve 19 so as to increase the flow rate to the desired or target flow rate. Similarly, if the measured flow rate is above the target flow rate, controller 22 controls the oxygen delivery valve 19 so as to decrease the flow rate to the desired or target flow rate.

In one embodiment, flow sensor 23 is configured to measure a mass flow rate (e.g., number of oxygen molecules) and the mass flow rate is used to control opening and closing oxygen delivery valve 19 to deliver the oxygen-enriched gas from reservoir 18 to a user.

In another embodiment, instead of controlling portable oxygen concentrator 10 such that a constant number of oxygen molecules (mass flow) are being delivered to the user, flow of portable oxygen concentrator 10 may be adjusted such that the volumetric flow (i.e., in liters per minute) of oxygen delivered to the user is held constant regardless of changes in gas temperature or local ambient pressure. That is, mass flow rate from flow sensor 23 is converted into a volume flow rate using oxygen temperature measurement from oxygen gas temperature sensor 131 and the local ambient pressure measurement from local pressure sensor 133. The volume flow rate measurement is then used to control opening and closing oxygen delivery valve 19 to deliver the oxygen-enriched gas from reservoir 18 to a user. The volume flow rate measurement is compared with the target flow rate (e.g., set by the user), oxygen delivery valve 19 is controlled to maintain the target or desired flow rate.

As noted above, oxygen sensor 118 may be used to monitor the purity of the oxygen being delivered from reservoir 18. Changes in the oxygen purity may be affected by the condition of the sieve material within sieve beds 12, the temperature and/or the humidity of the ambient air being drawn into portable oxygen concentrator 10 to charge sieve beds 12, and the like. Controller 22 may have a set target oxygen purity stored in memory and may monitor the purity detected by oxygen sensor 118. If the oxygen purity decreases below the target oxygen purity, controller 22 may increase the target reservoir pressure to compensate and increase the oxygen purity.

Use of piezo-electric proportional oxygen delivery valve 19 with closed loop (feed-back) control via mass flow sensor 23 allows portable oxygen concentrator 10 to deliver oxygen in either continuous flow or pulse flow waveforms. This arrangement also allows portable oxygen concentrator 10 to use a single delivery valve or circuit to deliver both continuous flow and pulse flow waveforms of dynamically controllable flow and delivery time. Temperature and pressure compensation may be used to convert portable oxygen concentrator 10 from a constant mass delivery system to a constant volumetric delivery system. This allows portable oxygen concentrator 10 to use a very low power delivery valve and a single delivery circuit which significantly saves on power consumption and size/weight of portable oxygen concentrator 10.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and does not impose any limits, but, on the contrary, the disclosure is intended to cover modifications and equivalent arrangements that are within the spirit and scope of the appended claims. For example, it is to be understood that, to the extent possible, one or more features of any embodiment are contemplated to be combined with one or more features of any other embodiment.

What is claimed is:

1. A portable oxygen concentrator configured to operate in two or more modes of operation, the two or more modes of operation including a first mode of operation and a second mode of operation, wherein the first mode of operation includes pulse delivery of oxygen-enriched gas, and wherein the second mode of operation includes continuous delivery of oxygen-enriched gas, comprising:
    a plurality of sieve beds configured to absorb nitrogen from air, wherein the plurality of sieve beds includes a first sieve bed and a second sieve bed, wherein the first sieve bed includes a first upstream port and a first downstream port, wherein the second sieve bed includes a second upstream port and a second downstream port;
    an oxygen side balance valve coupled to the first downstream port and the second downstream port, the oxygen side balance valve configured to balance bed pressure in the first and second sieve beds;
    at least one reservoir, communicating with the first downstream port and the second downstream port, configured to store oxygen-enriched gas exiting from the first downstream port and the second downstream port;
    a compressor configured to deliver air at one or more desired pressures to the first upstream port and the second upstream port;
    a proportional oxygen delivery valve communicating with the reservoir via a delivery deliver the oxygen-enriched gas;
    a mass flow sensor configured to generate a signal conveying a flow measurement of a mass flow rate of the oxygen-enriched gas through the delivery line;
    an oxygen sensor configured to generate an oxygen signal conveying a measurement of oxygen-concentration in the delivery line; and
    a controller configured to control a degree of opening and closing of the proportional oxygen delivery valve to deliver the oxygen-enriched gas from the reservoir to the user, based on the mass flow measurement and the oxygen-concentration measurement, at a constant mass of oxygen,
    wherein the controller is further configured to control the degree of opening and closing of the proportional oxygen delivery valve to deliver the oxygen-enriched gas from the reservoir to the user at a constant volume of oxygen-enriched gas based on the mass flow measurement and based on ambient pressure, and
    wherein the controller is further configured such that, while the portable oxygen concentrator operates in the first mode of operation, the oxygen-enriched gas is delivered through the proportional oxygen delivery valve in pulses timed to respiratory activity of the user, and while the portable oxygen concentrator operates in the second mode of operation, the oxygen-enriched gas is delivered continuously through the proportional oxygen delivery valve, and wherein the controller is configured to increase a target reservoir pressure responsive to the measured oxygen-concentration being below a concentration threshold value.

2. The portable oxygen concentrator of claim 1, further comprising a pressure sensor configured to generate a pressure signal conveying a pressure measurement of a pressure in the delivery line, wherein the controller is further configured to base delivery of the oxygen-enriched gas, while the portable oxygen concentrator operates in the first mode of operation, on the pressure signal generated by the pressure sensor.

3. The portable oxygen concentrator of claim 1, further comprising:
    an ambient pressure sensor configured to generate an ambient pressure signal conveying an ambient measurement of the ambient pressure; and
    a temperature sensor configured to generate a temperature signal conveying a temperature measurement of a temperature in the delivery line, wherein the controller is further configured to deliver a constant volume of oxygen-enriched gas based on the ambient pressure measurement, and the temperature measurement.

4. The portable oxygen concentrator of claim 1, wherein the proportional oxygen delivery valve is a piezo-electric valve.

5. A method for concentrating oxygen using two or more modes of operation, the two or more modes of operation including a first mode of operation and a second mode of operation, wherein the first mode of operation includes pulse delivery of oxygen-enriched gas timed to respiration activity of a user, and wherein the second mode of operation includes continuous delivery of oxygen-enriched gas, the method comprising:
    providing a portable apparatus configured to operate in the two or mode modes of operation, the portable apparatus comprising: a plurality of sieve beds, wherein the plurality of sieve beds includes a first sieve bed and a second sieve bed, wherein the first sieve bed includes a first upstream port and a first downstream port, wherein the second sieve bed includes a second upstream port and a second downstream port, an oxygen side balance valve coupled to the first downstream port and the second downstream port, the oxygen side balance valve configured to balance bed pressure in the first and second sieve beds, a reservoir storing oxygen-enriched gas exiting from the first downstream port and the second downstream port, a compressor, a proportional oxygen delivery valve communicating with the reservoir via a delivery line to deliver the oxygen-enriched gas through the proportional oxygen delivery valve, a mass flow sensor associated with the delivery line, an oxygen sensor associated with the delivery line, and control electronics adapted to control operation of the proportional oxygen delivery valve to deliver the oxygen-enriched gas at a constant mass of oxygen, the control electronics being further configured such that, while the portable apparatus operates in the first mode of operation, the oxygen-enriched gas is delivered through the proportional oxygen delivery valve in pulses timed to respiratory activity of a user, and while the portable apparatus operates in the second mode of operation, the oxygen-enriched gas is delivered continuously through the proportional oxygen delivery valve;

generating a signal conveying a flow measurement, by the mass flow sensor, of a mass flow rate of the oxygen-enriched gas through the delivery line;

generating a signal conveying a measurement, by the oxygen sensor, of oxygen-concentration in the delivery line;

controlling, using the control electronics, a degree of opening and closing of the proportional oxygen delivery valve to deliver the oxygen-enriched gas from the reservoir to the user based on the flow measurement and the oxygen-concentration measurement; and controlling, using the control electronics, the degree of opening and closing of the proportional oxygen delivery valve to deliver the oxygen-enriched gas from the reservoir to the user at a constant volume of oxygen-enriched gas based on the mass flow measurement and based on ambient pressure, and wherein controlling comprises increasing a target reservoir pressure responsive to the measured oxygen-concentration being below a concentration threshold value.

6. The method of claim 5, further comprising:
generating a pressure signal conveying a pressure measurement of a pressure in the delivery line, wherein controlling the degree of opening and closing of the proportional oxygen delivery valve is performed, while the portable apparatus operates in the first mode of operation, to base delivery of pulses of oxygen-enriched gas from the reservoir to the user on the signal generated by the flow sensor and the pressure signal.

7. The method of claim 5, further comprising:
generating, with a ambient pressure sensor, an ambient pressure signal conveying an ambient measurement of the ambient pressure;
generating, with a temperature sensor, a temperature signal conveying a temperature measurement of a temperature in the delivery line,
wherein controlling the degree of opening and closing of the proportional oxygen delivery valve to deliver the oxygen-enriched gas at the constant volume of oxygen-enriched gas is based on the ambient pressure measurement and the temperature measurement.

8. The method of claim 5, wherein the proportional oxygen delivery valve is a piezo-electric valve.

9. A system configured to concentrate oxygen using two or more modes of operation, the two or more modes of operation including a first mode of operation and a second mode of operation, wherein the first mode of operation includes pulse delivery of oxygen-enriched gas timed to respiration activity of a user, and wherein the second mode of operation includes continuous delivery of oxygen-enriched gas, the system comprising:

compressing means for generating a supply of compressed air from a supply of air;

separating means for providing a supply of oxygen-enriched gas from the supply of compressed air, the separating means configured to absorb nitrogen from air, wherein the separating means include a first sieve bed and a second sieve bed, wherein the first sieve bed includes a first upstream port and a first downstream port, wherein the second sieve bed includes a second upstream port and a second downstream port;

an oxygen side balance valve coupled to the first downstream port and the second downstream port, the oxygen side balance valve configured to balance bed pressure in the first and second sieve beds;

oxygen storing means for storing the oxygen-enriched gas;

proportional valve means configured to communicate with the oxygen storing means through a delivery line to deliver the oxygen-enriched gas through the proportional valve means;

sensing means for generating a signal conveying a mass flow measurement of a mass flow rate of the oxygen-enriched gas through the delivery line;

sensing means for generating a signal conveying an oxygen measurement of an oxygen-concentration in the delivery line; and means for controlling a degree of opening and closing of the proportional valve means to deliver the oxygen-enriched gas at a constant mass of oxygen to the user, wherein the means for controlling is further configured to change the delivery mode from a constant mass of oxygen to a delivery mode having a constant volume of oxygen-enriched gas based on ambient pressure, and wherein operation of the means for controlling is based on the flow measurement and the oxygen-concentration measurement, wherein the means for controlling is further configured such that, while the system operates in the first mode of operation, the oxygen-enriched gas is delivered through the proportional valve means in pulses timed to respiratory action of a user, and while the system operates in the second mode of operation, the oxygen-enriched gas is delivered continuously through the proportional valve means, and wherein the means for controlling is configured to increase a target reservoir pressure responsive to the measured oxygen-concentration being below a concentration threshold value.

10. The system of claim 9, wherein the proportional valve means is a piezo-electric valve.

11. The system of claim 9, further comprising:
means for generating an ambient pressure signal conveying an ambient measurement of the ambient pressure;
means for generating a temperature signal conveying a temperature measurement of a temperature in the delivery line;
wherein the means for controlling the degree of opening and closing of the proportional valve means is configured to deliver the oxygen-enriched gas at the constant volume of oxygen-enriched gas based on the ambient pressure measurement and the temperature measurement.

* * * * *